United States Patent [19]

Shiragami et al.

[11] Patent Number: 5,625,057
[45] Date of Patent: Apr. 29, 1997

[54] PROCESS FOR PREPARING 2',3'-DIDEOXY-2',3'-DEHYDRONUCLEOSIDES

[75] Inventors: Hiroshi Shiragami; Yumiko Uchida; Kunisuke Izawa, all of Kawasaki, Japan

[73] Assignee: Ajinomoto Co., Inc., Tokyo, Japan

[21] Appl. No.: 295,478

[22] Filed: Aug. 25, 1994

Related U.S. Application Data

[63] Continuation of Ser. No. 899,906, Jun. 17, 1992, abandoned.

[30] Foreign Application Priority Data

Jun. 19, 1991 [JP] Japan .................................. 3-245290

[51] Int. Cl.⁶ .......................... C07H 1/00; C07H 19/073
[52] U.S. Cl. .............................. 536/55.3; 536/28.2
[58] Field of Search ............................ 536/55.3, 28.2

[56] References Cited

U.S. PATENT DOCUMENTS

| | | |
|---|---|---|
| 4,835,104 | 5/1989 | Yokozeki et al. |
| 4,904,770 | 2/1990 | Starrett, Jr., et al. |
| 5,200,514 | 4/1993 | Chu .................................. 536/28.53 |
| 5,290,927 | 3/1994 | Honda et al. ...................... 536/27.6 |
| 5,310,895 | 5/1994 | Shiragami et al. ................. 536/27.14 |
| 5,336,770 | 8/1994 | Shiragami et al. ..................... 544/276 |

OTHER PUBLICATIONS

Patent Abstracts of Japan, vol. 13, No. 72 (C–570)(3420), Feb. 17, 1989, & JP-63-264-596, Nov. 1, 1988, Hiroshi Shiragami, et al., "Production of Didehydronucleosides".
Patent Abstracts of Japan, vol. 9, No. 166 (C–290)(1889), Jul. 11, 1985 & JP-60-38-395, Feb. 27, 1985, Takao Takahara, et al., "Preparation of 5-Fluorocytidine".
The Journal of Organic Chemistry, vol. 54, pp. 4780–4785, 1989, M. M. Mansuri, et al., "Preparation of 1–(2, 3–Dideoxy–β–D–Glycero–Pent–2–Enofuranosyl) Thymine (d4T)[1] and 2',3'–Dideoxyadenosine (dda) . . . ".

*Primary Examiner*—Gary L. Kunz
*Attorney, Agent, or Firm*—Oblon, Spivak, McClelland, Maier & Neustadt, P.C.

[57] ABSTRACT

A process for preparing a 2', 3'-dideoxy-2',3'-didehydropyrimidine nucleoside comprising reacting the pyrimidine ribofuranoside with a trialkyl orthoester to yield the 2',3'-O-alkoxyethylidene derivative; which is reacted with hydrogen bromide in acetic acid or acetyl bromide to yield the 2-deoxy-2'-bromo-3'-acetyl-pyrimidine nucleoside; which is then reduced with zinc to yield the 2',3'-olefin of the pyrimidine nucleoside.

3 Claims, No Drawings

PROCESS FOR PREPARING 2',3'-DIDEOXY-2',3'-DEHYDRONUCLEOSIDES

This application is a continuation of application Ser. No. 07/899,906, filed on Jun. 17, 1992, now abandoned.

BACKGROUND OF THE INVENTION

1. Field of the Invention

The present invention provides a process for producing a 2',3'-dideoxy-2',3'-didehydronucleoside derivative, which is useful as an antiviral agent etc., and intermediates for the production thereof.

2. Discussion of the Background d4T [1-(2,3-dideoxy-β-D-glycero-pent-2-enofuranosyl) thymine] represented by the formula (XII):

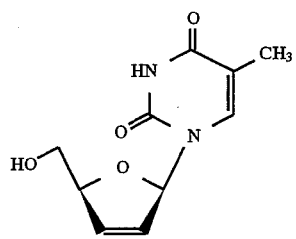

(XII)

is a 2',3'-dideoxy-2',3'-didehydro nucleoside derivative, and has antiviral activity both in vitro and in vivo. Especially, its anti-HIV activity is equivalent to AZT (3'-azido-3'-deoxythymidine) which is the first drug that has been approved in USA for the treatment of HIV infection. As regards anti-HIV activity, see M. M. Mansuri et al., Antimicrob. Agents Chemother., 34(4), 637–41 (1990); Y. Hamamoto et al., Antimicrob. Agents Chemother., 31(6), 907–910 (1987); and M. Baba et al., Biochem. Biophys. Res. Commun., 142(1), 128–34 (1987). As regards, anti-HBV activity, see E. Matthes et al., Antimicrob. Agents. Chemother., 34(10), 1986–90 (1990).

As for the production of d4T from thymidine as a raw material, there are known a process via an oxetane analogue (J. C. Martin et al., Nucleosides Nucleotides, 8(5–6), 841–4 (1988), and M. M. Mansuri et al., J. Med. Chem., 32(2) 461–6 (1989)), and a process using selenium oxidation (M. J. Vial et al., Nucleosides Nucleotides, 9(2) 245–58 (1990)). Also is known a process using glycosylation reaction (L. J. Willson et al., Tetrahedron Lett., 31 (13), 1815, (1990), and C. K. Chu et al., J. Org. Chem., 55(5) 1418–20 (1990)). Every process has, however, disadvantageous aspects such as expensiveness of thymidine as a raw material, use of reagents difficult of commercial handling (poisonous or dangerous), difficulty in obtaining d4T in high yields, and the like. As for the synthesis of d4T from 5-methyluridine, processes utilizing radical reduction (C. K. Chu et al., J. Org. Chem., 54(9), 2217–25 (1989), and M. M. Mansuri et al., J. Org. Chem., 54(20), 4780 (1989),) are known. They are, however, not commercially favorable in reagents employed, reaction condition, etc.

In 1974, Marumoto et al. developed a process for the synthesis of 2'-deoxy-2'-bromo-3',5'-O-diacetyluridine represented by the formula (XIII):

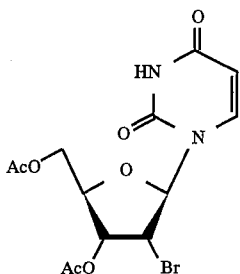

(XIII)

by reacting uridine with acetyl bromide (AcBr). See Chem. Pharm. bull., 22(1) 128–34 (1974).

Mansuri et al. applied the above process per se to 5methyluridine represented by the formula (XIV):

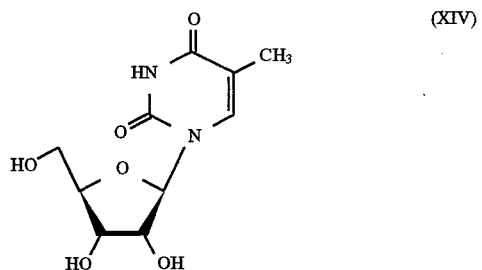

(XIV)

and, by reacting 5-methyluridine with AcBr, synthesized 2'-deoxy-2'-bromo-3',5'-O-diacetyl-5-methyluridine represented by the formula (XV):

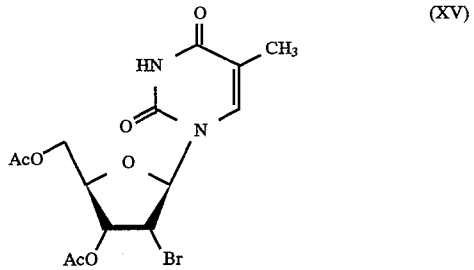

(XV)

The resultant compound of the formula (XV) is then reacted with zinc-copper couple (hereinafter, abbreviated as Zn-Cu) to give the corresponding olefin. Thus, the synthesis of d4T was completed. See M. M. Mansuri et al., J. Org. Chem., 54(20), 4780(1989).

On the other hand, the present inventors had studied, prior to Mansuri et al, synthesis of 2'-deoxy-2'-bromo-3',5'-O-diacetyl-5-methyluridine of the formula (XV) by reacting 5-methyluridine with AcBr as an advantageous commercial synthetic process of d4T from 5-methyluridine. Reaction conditions were studied extensively, and it was found that yields are low, and many by-products are produced.

Furthermore, they had also studied β-elimination of 2'-deoxy-2'-bromo-3',5'-O-diacetyl-5-methyluridine into the olefin and found various serious problems in known methods, such as unstableness of Zn-Cu, too much required amounts of Zn-Cu, low reaction yield, required complicated removal procedures of the Zn salt after the reaction (removal procedures in combination of resin purification using a chelate resin or an ion-exchange resin and filtration using celite, etc.), and so on.

SUMMARY OF THE INVENTION

Accordingly, an object of the present invention is to provide a novel commercially advantageous process for the synthesis of 2',3'-dideoxy-2',3'-didehydronucleoside derivatives and to provide synthetic intermediates therefor. Other objects will become apparent from the description of the invention given hereinbelow.

The present invention thus provides a novel synthetic process for producing 2',3'-dideoxy-2',3'-didehydronucleoside derivatives useful as virucides, and novel intermediates for their synthesis, which process comprising reacting a nucleoside derivative such as 5-methyluridine with a trialkyl orthoacetate (MeC(OR)₃) in acetic acid to convert the nucleoside derivative into a 2',3'-O-alkoxyethylidene-nucleoside compound, which is then isolated or not isolated, followed by the reaction with a hydrogen bromide in acetic acid and/or acetyl bromide, followed by converting into the olefin by adding zinc powder, whereby formation of by-products such as those brominated at the 5'-position, thymine, and the triacetyl derivatives is inhibited, and nucleoside derivatives such as 2'-deoxy-2'-bromo-3',5'-O-diacetyl-5-methyluridine and, therefore, the object compounds 2',3'-dideoxy-2',3'-didehydronucleoside derivatives can be obtained in high yields.

DETAILED DESCRIPTION OF THE INVENTION

In order to attain the objects, the present inventors first tried to clarify the by-products in application of the process reported by Marumoto et al. in which 2'-deoxy-2'-bromo-3',5'-O-diacetyl-5-methyluridine is synthesized by reacting 5-methyluridine with AcBr. As the results, it was found that 2',3',5'-O-triacetyl-5-methyluridine shown by the formula (XVI):

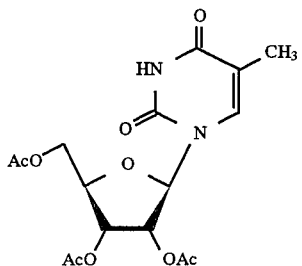

(XVI)

which results from acetylation of all the hydroxyl groups of 5-methyluridine, thymine formed by elimination of the glycose moiety, another by-product which results from bromination of the 5'-position and shown by the formula (XVII):

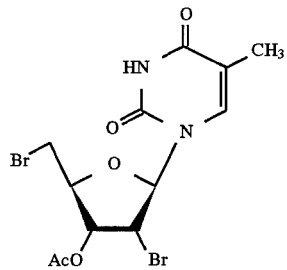

(XVII)

and others are produced.

In particular, it was found that formation of the by-product shown by the formula (XVII) not only decreases the yield of 2'-deoxy-2'-bromo-3',5'-O-diacetyl-5-methyluridine but also makes it difficult to purify d4T obtained by further reactions.

It was thought that since the by-products had been identified, the mechanism of the side-reaction would become clear, and on the basis of the mechanism, in turn, the way of reducing the by-products and improving yields of the object product would be found.

From the analysis of the by-products, it is considered that the reaction of AcBr with 5-methyluridine to give 2'-deoxy-2'-bromo-3',5'-diacetoxy-5- methyluridine proceeds with the mechanism illustrated in Scheme 1 below.

Scheme 1

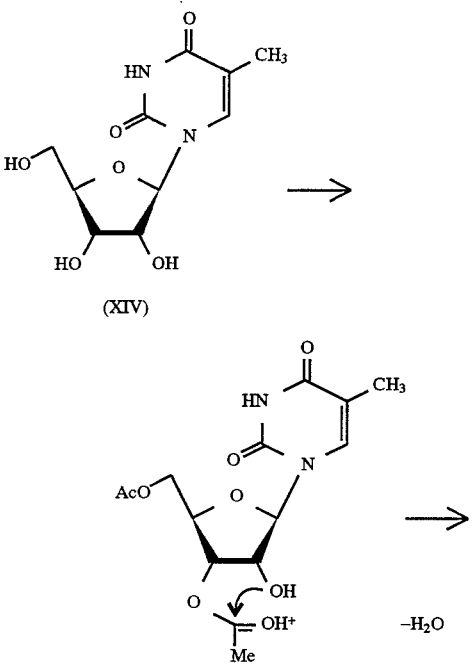

-continued
Scheme 1

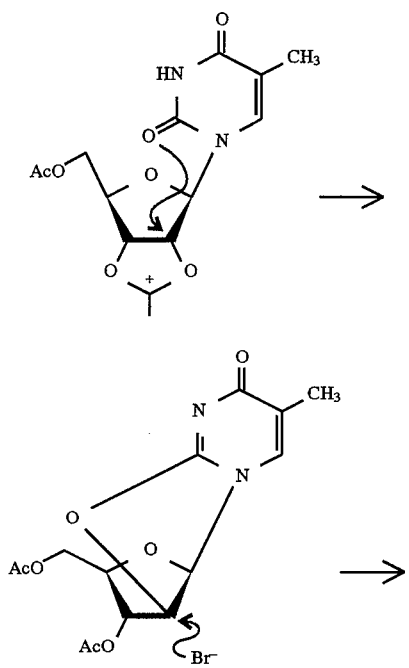

-continued
Scheme 1

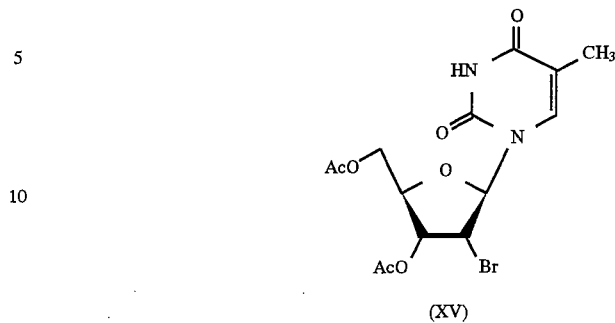

(XV)

The by-product of the formula (XVII) has a similar structure to the desired product (XV) as for the 2' and 3'-positions of the glycose moiety, that is, 2'-Br and 3'-OAc. This means that the introduction of 2'-Br and 3'-OAc groups into glycose moiety might proceed through the same mechanism for both products. It has also been confirmed that the desired product has not been converted into the by-product under the reaction conditions. We postulate a mechanism shown in Scheme 2a in which the reaction of 5-methyluridine with AcBr gives a 5'-free derivative as a by-product which easily affords 5'-cyclonucleosides leading to the 5'-Br product (XVII).

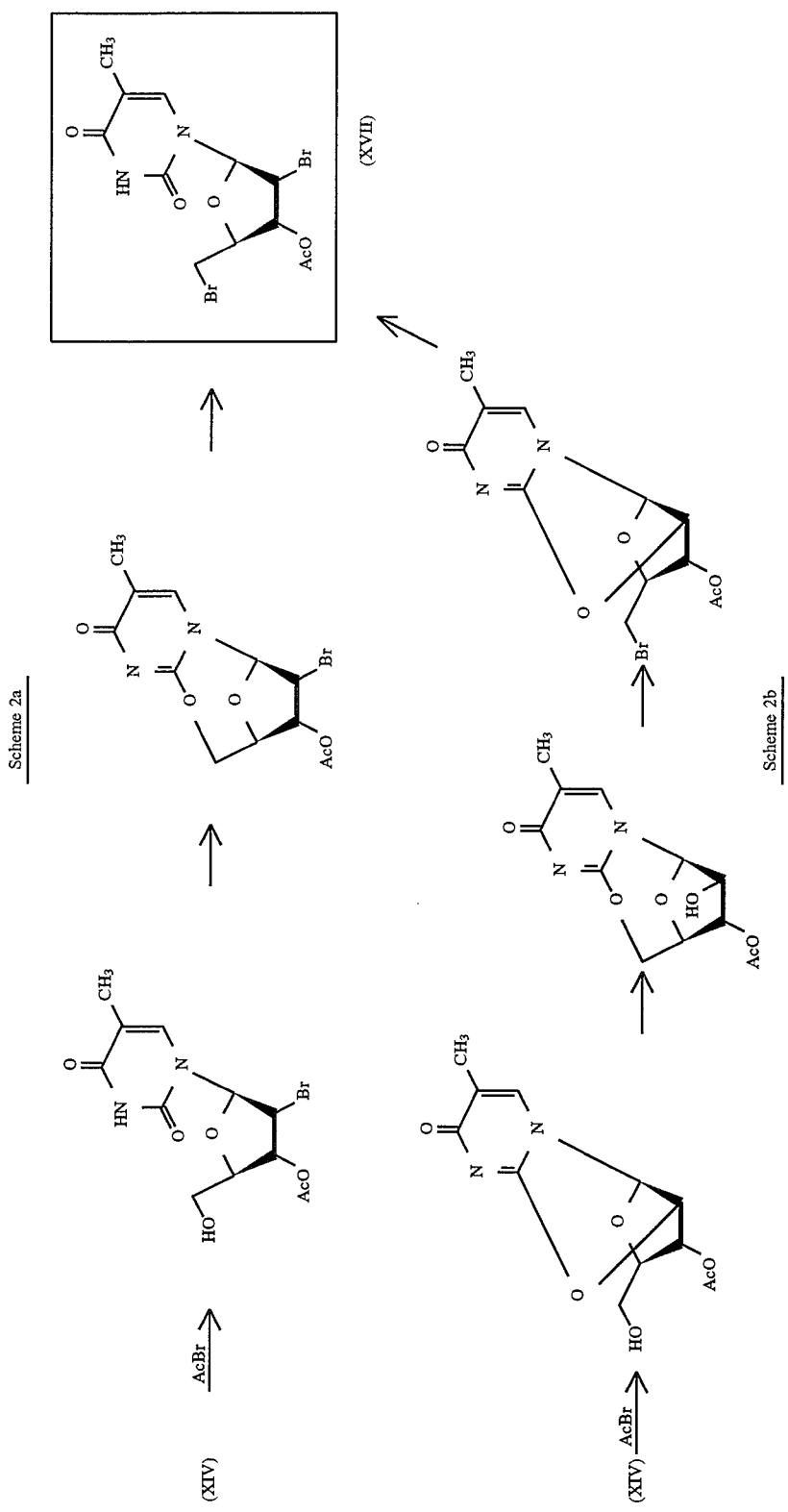

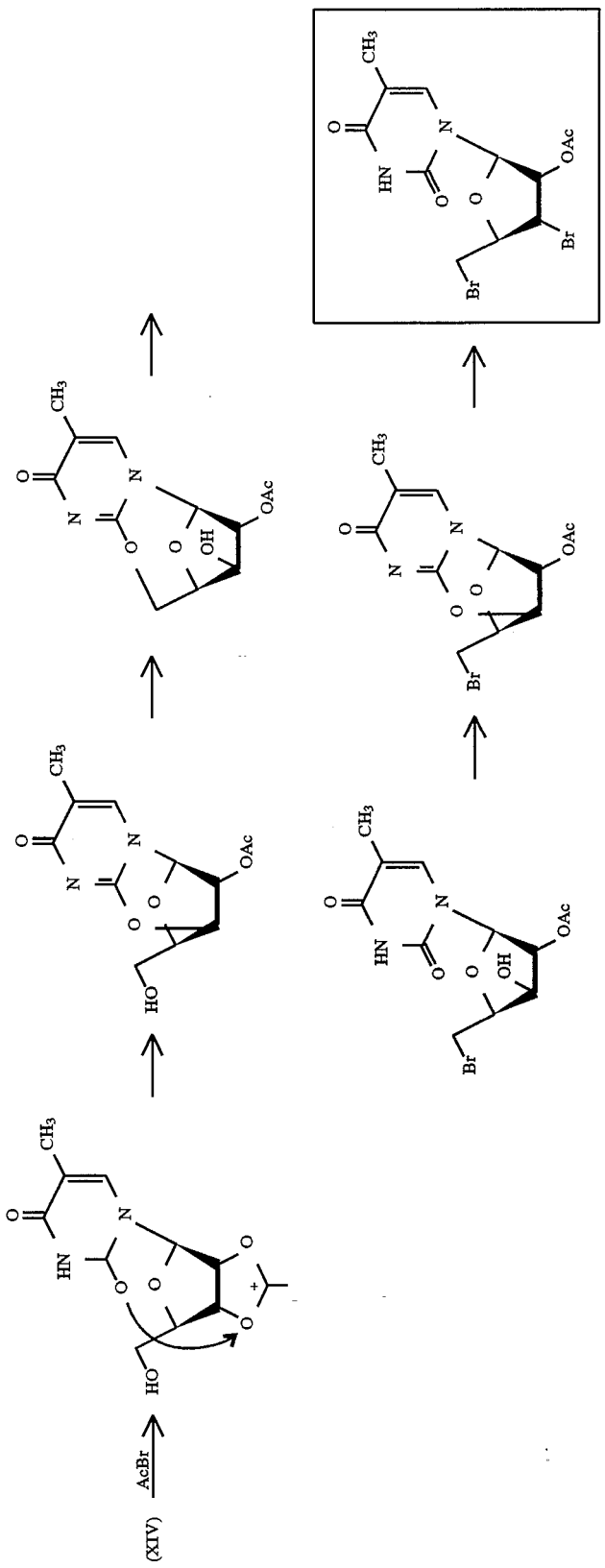

The fact that addition of water or alcohol which may prevent the acetylation of the 5'-position increased the formation of by-product strongly supports the postulated mechanism. On the other hand, the direct reaction of 5-methyluridine with AcBr according to the process of Marumoto et al. produces in situ water during the reaction as is apparent from Scheme 1.

Therefore, the present inventors have studied various synthetic processes wherein compounds of different structures are used not to produce any water in the reaction system, and found as the results that employing nucleoside derivatives, novel compounds, shown by the formula (I):

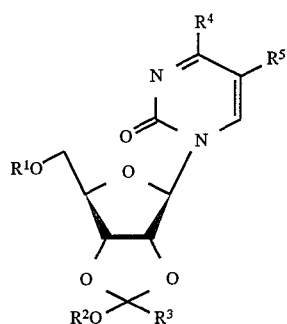

and reacting therewith hydrogen bromide in acetic acid and/or acetyl bromide produces nucleoside derivatives shown by the formula (IV):

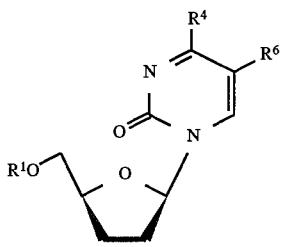

in high yields, inhibiting formation of thymine and other by-products of the formulae (XVI) and (XVII), as is illustrated in Scheme 3 wherein 5-methyluridine is employed as an example. Thus, the present invention has been completed.

Scheme 3

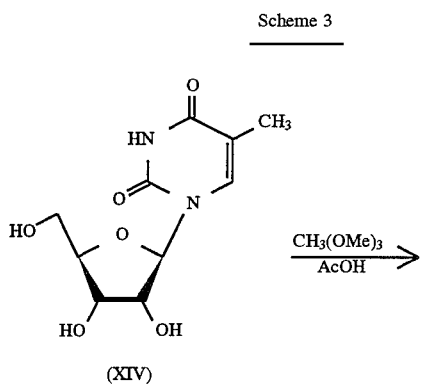

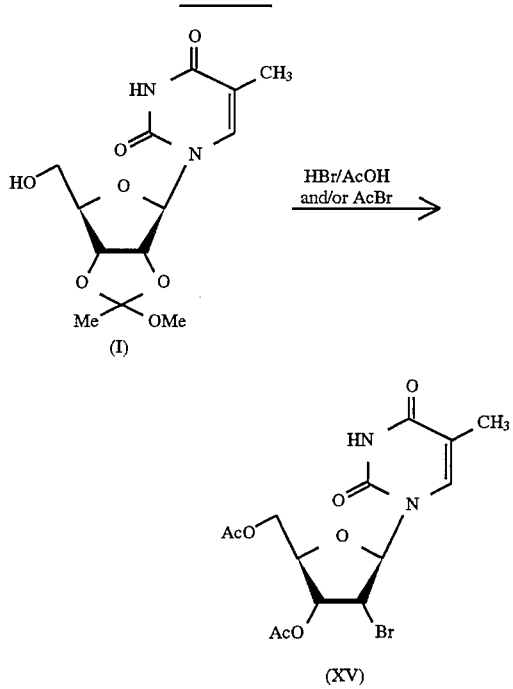

That is, the present invention relates to novel nucleoside derivatives represented by the general formula (I), and a production process thereof, and also relates to novel processes for producing other nucleoside derivatives utilizing the novel nucleoside derivatives as the intermediate.

The nucleoside derivatives to be used as a starting material according to the present invention have, as the base part, a pyrimidine group bound at the 1-position to the glycose moiety. The pyrimidine group may be substituted. Examples include the uracil group, the cytosine group, and uracil groups and cytosine groups substituted by alkyl group(s) having from 1 to 12 carbon atoms or by halogen atom(s). The hydroxyl group or amino group in the uracil group or cytosine group may be protected. The protecting groups generally include an acyl group, an organosilyl group, and an alkyl group.

More specifically, a nucleoside derivative represented by the formula (II):

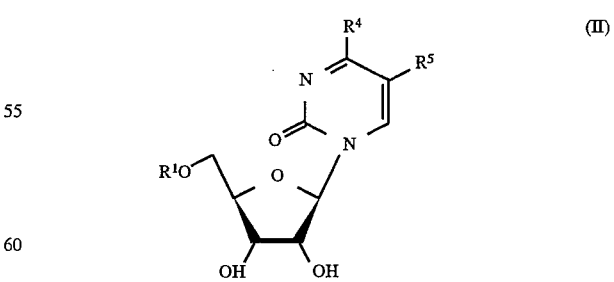

such as 5-methyluridine is reacted in acetic acid with an orthoester of an organic acid such as trialkyl orthoacetate (MeC (OR) 3) to obtain a 2',3'-O-alcoxyethylidene-nucleoside compound represented by the formula (I) or (III):

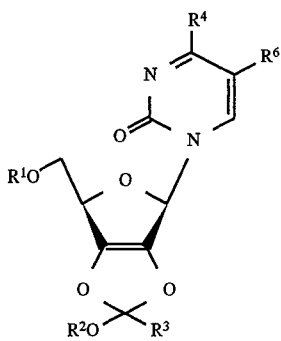

The compound after separated from the reaction mixture or the reaction mixture per se preferably after concentrated under reduced pressure is reacted with hydrogen bromide in acetic acid and/or acetyl bromide, whereby a nucleoside derivative represented by the formula (VI):

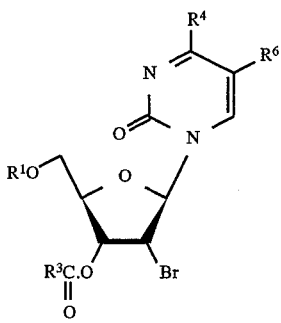

such as 2'-deoxy-2'-bromo-3',5'-O-diacetyl-5-methyluridine in a high yield, formation being inhibited of by-products such as those brominated at the 5'-position, thymine, and triacetyl compounds.

According to the present invention, synthesis of a 2',3'-O-alkoxyethylidene-nucleoside compound represented by the formula (I) is carried out by reacting in acetic acid a nucleoside derivative represented by the formula (II) such as 5-methyluridine with an orthoester of an organic acid. Examples of the esters of orthocarboxylic acids which may be employed include orthoacetate esters, more specifically, alkyl esters in respect of which the alkyl group has from 1 to 6 carbon atoms such as the methyl ester and ethyl ester. Esters of orthopropionic acid and orthobenzoic acid may also be employed. The present synthetic process wherein an orthoacetate ester is reacted in acetic acid is advantageous because the by-products which cause lower yields in the next step may be reduced only by concentration following the reaction, in contrast with a conventional process wherein an acid catalyst such as p-toluenesulfonic acid is employed and operation such as extraction is required following the reaction.

Proper amounts of the orthoacetate ester employed are 1–2 equivalents based on the nucleoside derivative. Reaction temperatures are 10°–60° C. and reaction periods of time are from 30 minutes to 24 hours.

A 2',3'-O-alkoxyethylidene-nucleoside compound represented by the formula (I) according to the present invention can be converted into a nucleoside derivative represented by the formula (VI) by reaction with hydrogen bromide in acetic acid and/or acetyl bromide.

The bromide source employed may be either hydrogen bromide in acetic acid or acetyl bromide, making the reaction proceed in a high yield. As regards the case of hydrogen bromide in acetic acid, it is noted that addition of acetic anhydride improves yields. A mixture of hydrogen bromide in acetic acid and acetyl bromide gives the highest yields.

Proper amounts of hydrogen bromide or acetyl bromide employed are 1–4 equivalents based on the nucleoside derivative. Smaller amounts than 1 equivalent will not move the reaction forward while larger amounts than 4 equivalents will increase the production of by-products, thus both are not preferable. Reaction temperatures are 0°–100° C. and reaction periods of time are from 30 minutes to 24 hours.

Although a nucleoside derivative represented by the formula (VI) may be isolated once followed by converting into the olefin with Zn powder, simply subsequent addition of Zn powder in an amount of 2.5–3 equivalents based on the nucleoside derivative without isolation will move the reaction forward to the olefin to produce a 2',3'-dideoxy-2',3'-didehydronucleoside derivative represented by the formula (IV).

In Scheme 4, an example for d4T is illustrated.

Scheme 4

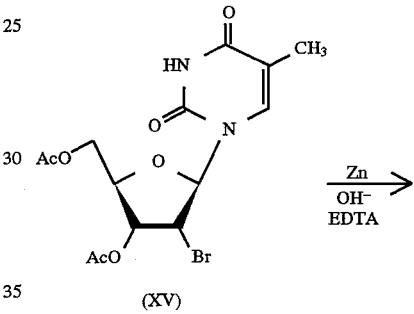

Amounts of Zn powder employed are 1–5 equivalents. Smaller amounts than 1 equivalent will leave raw materials unreacted considerably while larger amounts than 5 equivalents will make the removal operation complicated, thus both are not preferable. Reaction temperatures are 0°–30° C., and reaction periods of time are from 30 minutes to 24 hours.

After the reaction, the Zn moiety can be removed with sodium ethylenediaminetetraacetate, e.g., by washing the reaction mixture with an aqueous solution of the Na salt of ethylenediaminetetraacetic acid (EDTA), the pH of the solution being 3–9. Amounts of EDTA are preferably 1–4 equivalents based on the Zn moiety. Smaller amounts than 1 equivalent will not remove the Zn moiety while larger amounts than 4 equivalents will increase the amount of washing water layer, thus both are not preferable.

Following the removal of the Zn moiety, the 2',3'-dideoxy-2',3'-didehydronucleoside derivative is obtained. If required, the protecting group at the 5'-position is removed. How to remove depends on the protecting group; for the case of an acyl group, saponification with an alkali is a usual manner.

By way of common purification procedures such as purification using an adsorption resin and crystallization, the 2',3'-dideoxy-2',3'-didehydronucleoside derivative can be isolated.

A 2',3'-dideoxy-2',3'-didehydronucleoside derivative can be produced also by employing a nucleoside derivative represented by the formula (II) as the raw material and reacting it with a trialkyl orthoacetate to produce an alkoxyethylidene-nucleoside derivative represented by the formula (I), which is then, without isolation, allowed to react with hydrogen bromide in acetic acid and/or acetyl bromide to produce a brominated nucleoside derivative represented by the formula (VI), which is further reacted into the olefin with Zn powder.

As explained, a nucleoside derivative represented by the formula (I) according to the present invention is useful as the intermediate for the synthetic process of 2',3'-dideoxy-2',3'-didehydronucleoside derivatives typically represented by d4T, and a novel commercially advantageous synthetic process is provided.

Examples:

Hereunder will be given more detailed explanation of the invention with reference to examples.

Example 1: Synthesis of 2',3'-O-methoxyethylidene-5-methyluridine (I) from 5-methyluridine (II, XIV).

To 2.58 g of 5-methyluridine in 5 ml (8.7 eg.) of acetic acid was added 1.73 ml (1.4 eq.) of trimethyl orthoacetate and allowed to react at 50° C. for 1 hour.

Thereafter, the reaction mixture was concentrated under reduced pressure. After chloroform was added to the residue, the mixture was washed with saturated brine, and the organic layer was separated and concentrated. Purification by silica gel column chromatography (eluent: CHCl$_3$/MeOH) gave 3.0 g of 2',3'-O-methoxyethylidene-5-methyluridine (a mixture of two diastereoisomers A and B) as white crystals. Yield, 95%.

$^1$HNMR (300 MHz, CDCl$_3$) analytical values:

A δ: 1.93 (s, 3H, CH$_3$), 2.19 (s, 3H, CH$_3$), 3.27 (s, 3H, OCH$_3$), 3.92 (m, 2H, H-5' ab), 4.38 (m, 1H, H-4'), 5.14 (m, 1H, H-3'), 5.17 (m, 1H, OH), 5.49 (d, 1H, J=2.8 Hz, H-2'), 5.66 (d, 1H, J=3.0 Hz, H-1'), 7.12 (s, 1H, H-6).

B δ: 1.59 (s, 3H, CH$_3$), 2.17 (s, 3H, CH$_3$), 3.38 (s, 3H, OCH$_3$), 3.96 (m, 2H, H-5' ab), 4.24 (m, 1H, H-4'), 5.06 (m, 1H, H-3'), 5.17 (m, 1H, OH), 5.63 (d, 1H, J=3.0 Hz, H-2'), 5.69 (d, 1H, J=3.1 Hz, H-1'), 7.13 (s, 1H, H-6).

Mass spectrum analytical value: MH$^+$=315.

Example 2: Synthesis of 2'-deoxy-2'-bromo-3',5'-O-diacetyluridine (VI) from uridine (II).

To 2.45 g of uridine in 5 ml (8.7 eq.) of acetic acid was added 1.78 ml (1.4 eq.) of trimethyl orthoacetate and allowed to react at 50° C. for 1 hour. Thereafter, the reaction mixture was concentrated under reduced pressure. After 20 ml of acetonitrile was added to the residue, a mixture of 5.39 g (2 eq.) of HBr in acetic acid (30%) and 1.48 ml (2 eq.) of acetyl bromide was added dropwise with stirring at 60° C. It was confirmed by high performance liquid chromatography (HPLC) that the reaction was completed after 5 hours.

The reaction mixture was added dropwise to 10 ml of ice-cooled water, while the pH was kept at 7 by adding aqueous 25% sodium hydroxide solution. After finishing the addition, the organic layer was separated and the solvent was removed therefrom by distillation under reduced pressure to obtain 4.81 g of brown oily product.

HPLC analysis revealed that 3.42 g 2'-deoxy-2'-bromo-3',5'-O-diacetyluridine had been produced. Yield, 87.8%.

$^1$HNMR (300MHz, CDCl$_3$) analytical values:

δ: 2.14 (s, 3H, CH$_3$), 2.19 (s, 3H, CH$_3$), 4.38 (m, 2H, H-5' ab), 4.42 (m, 1H, H-4'), 4.61 (dt, 1H, J=5.7 Hz, H-2'), 5.14 (dd, 1H, J=5.5 Hz, H-3 '), 5.81 (d, 1H, J=8.1 Hz, H-5), 6.20 (d, 1H, J=5.5 Hz, H-1'), 7.46 (d, 1H, J=8.0 Hz, H-6).

Mass spectrum analytical value: MH$^+$=391.

Example 3: Synthesis of 2'-deoxy-2'-bromo-3',5'-O-diacetyl 5-methyluridine (VI) from 5-methyluridine (II, XIV).

To 5 g (19.38 mmol) of 5-methyluridine in 10 ml of acetic acid was added 3.45 ml (1.4 eq. ) of MeC (OMe)$_3$ and allowed to react at 50° C. for 1 hour. The reaction mixture was concentrated to 8.5 g under reduced pressure. HPLC analysis revealed that 2',3'-O-methoxyethylidene-5-methyluridine in acetic acid had been obtained in a yield of 95%.

To the solution was added 40 ml of acetonitrile, the resulting solution was heated to 50° C. and at the temperature, a mixture of 15.7 g (3 eq.) of 30% HBr/AcOH and 1.43 ml (1 eq.) of AcBr was added dropwise thereto over 1 hour. The reaction temperature was raised to 60° C. and the reaction was allowed to continue for further 4 hours. The reaction mixture was then cooled to 10° C. and 10 ml of water was added thereto, followed by neutralization with aqueous 25% sodium hydroxide. The organic layer was separated by extraction.

HPLC revealed that 7.54 g (17.46 mmol) of 2'-deoxy-2'-bromo-3',5'-O-diacetyl-5-methyluridine had been produced in a 90% yield from the 5-methyluridine.

$^1$HNMR ( 600 MHz, CDCl$_3$) analytical values:

δ: 1.97 (s, 3H, H-5), 2.17 (s, 3H), 2.21 (s, 3H) 4.38 (m, 3H, H-5' & H-4'), 4.54 (dd, 1H, J=6.1, 6.1 Hz, H-2'), 5.18 (dd, 1H, J=3.7, 6.1 Hz, H-3'), 6.22 (d, 1H, J=6.1 Hz, H-1'), 7.19 (s, 1H), 8.55 (brs, 1H).

Mass spectrum analytical value: MH$^+$=403, 405.

Example 4: Synthesis of 2'-deoxy-2'-bromo-3', 5'-O-diacetyl-5-methyluridine from 5-methyluridine.

To 5 g (19.38 mmol) of 5-methyluridine in 10 ml of acetic acid was added 3.45 ml (1.4 eq.) of MeC(OMe)$_3$ and allowed to react at 50° C. for 1 hour. The reaction mixture was concentrated to 8.5 g under reduced pressure. 2', 3'-O-methoxyethylidene-5-methyluridine in acetic acid was obtained.

To the solution was added 40 ml of acetonitrile, the resulting solution was brought to 50° C. and at the temperature, 4.29 ml (3 eq.) of AcBr was added dropwise thereto over 1 hour. The reaction temperature was raised to 60° C. and the reaction was allowed to react for further 4 hours. The reaction mixture was then cooled to 10° C. and 10 ml of water was added thereto, followed by neutralization with aqueous 25% sodium hydroxide. The organic layer was separated by extraction.

HPLC revealed that 6.34 g (15.70 mmol) of 2'-deoxy-2'-bromo-3',5'-O-diacetyl-5-methyluridine had been produced in a 81.0% yield from the 5-methyluridine.

Example 5: Synthesis of 2'-deoxy-2'-bromo-3',5'-O-diacetyl-5-methyluridine from 5-methyluridine.

To 5 g (19.38 mmol) of 5-methyluridine in 10 ml of acetic acid was added 3.45 ml (1.4 eq.) of MeC(OMe)$_3$ and allowed to react at 50° C. for 1 hour. The reaction mixture was concentrated to 8.51 g under reduced pressure to obtain 2',3'-O-methoxyethylidene-5-methyluridine in acetic acid.

To the solution was added 40 ml of acetonitrile the resulting solution was heated to 50° C., and at the temperature, a mixture of 15.7 g (3 eq.) of 30% HBr/AcOH and 1.83 ml of Ac$_2$O was added dropwise thereto over 1 hour. The reaction temperature was raised to 60° C. and the reaction was allowed to continue for further 4 hours. The reaction mixture was then cooled to 10° C. and 10 ml of water was added thereto, followed by neutralization with aqueous 25% sodium hydroxide. The acetonitrile layer was extracted.

HPLC revealed that 6.91 g (17.11 mmol) of 2'-deoxy-2'-bromo-3',5'-O-diacetyl-5-methyluridine had been produced in a 88.3% yield from the 5-methyluridine.

Example 6: Synthesis of d4T [1-(2,3-Dideoxy-β-D-glycero-pent-2-enofuranosyl)thymine](IV, XII) from 2'-deoxy-2'-bromo-3',5'-O-diacetyl-5-methyluridine (VI).

To 6.21 g (15.33 mmol) of 2'-deoxy-2'-bromo-3',5'-O-diacetyl- 5-methyluridine in acetonitrile was added 2.35 g (2.4 eq.) of Zn powder, and the mixture was stirred at room temperature for 2 hours.

It was confirmed by HPLC that the reaction had been completed. Then, to the reaction mixture was added an aqueous EDTA Na salt solution separately prepared (in the following way: 26.80 g of EDTA 2Na 2H$_2$O was added to 100 ml of water, and aqueous 25% sodium hydroxide solution was added thereto to make pH 7.9 to obtain a homogeneous solution; EDTA 2 eq. vs. Zn), and the resulting mixture was extracted with MeCN (50 ml×2). The organic layers were combined and concentrated, followed by addition of aqueous 25% sodium hydroxide solution to make pH 12.The aqueous solution was stirred for 30 minutes, and then aqueous HCl solution was added thereto to return the pH to 7.

HPLC revealed that 2.76 g (12.34 mmol) d4T of had been produced in the aqueous solution in a 80.5% yield. The resulting solution was purified using a synthetic adsorption resin to give d4T as white crystals.

$^1$H-NMR (300 MHz, CDCl$_3$) analytical values:

δ: 1.84 (s, 3H, CH$_3$), 3.87 (dd, 2H, J=4.3, 2.3 Hz, H-5'), 4.94 (s, 1H, H-4'), 5.85 (dd, 1H, J=1.0, 2.3 Hz, H-2'), 6.34 (d, 1H, J=6.3 Hz, H-3') , 7.04 (s, 1H, H-1') , 7.45 (d, 1H, H-6).

Mass spectrum analytical value: MH$^+$=225.

Example 7: Synthesis of 2'-deoxy-2'-bromo-3', 5'-O-diacetyl-5-methyluridine from 2',3'-O-methoxyethylidene-5-methyluridine.

From the 2',3'-O-methoxyethylidene-5-methyluridine obtained in Example 1 was synthesized 2'-deoxy-2'-bromo-3',5'-O-diacetyl-5-methyluridine and the results are shown in Table 1.

For the purpose of comparison, 5-methyluridine (II) was subjected to direct bromoacetylation (Comparative Examples), and the results were also shown in the table.

TABLE 1

Synthesis of 2'-deoxy-2'-bromo-3',5'-O-diacetyl-5-methyluridine from 2',3'-O-methoxyethylidene-5-methyluridine as the starting material

| No. | Bromoacetylation Reagent (eq.) | | | Yield[1] | By-products (%)[2] | | |
|-----|------|---------|-------|------|------|-------|---------|
|     | AcBr | HBr/AcOH | Ac$_2$O | (%) | (XVI) | (XVII) | Thymine |
| 1 | 3 | 1 | — | 90.5 | 2.6 | 0 | 6 |
| 2 | 2 | 2 | — | 90.0 | 1.8 | 1.3 | 4.7 |
| 3 | 1 | 3 | — | 91.0 | 1.5 | 1.9 | 4.5 |
| 4 | 0 | 4 | — | 81.2 | 1.6 | 2.2 | 4.3 |
| 5 | 0 | 4 | 1 | 81.7 | 2.2 | 1.5 | 3.9 |
| 6 | 0 | 3 | 1 | 88.3 | 2.0 | 1.3 | 4.8 |
| 7 | 3 | 0 | — | 81.0 | 3.6 | 0 | 10.3 |
| Comparative Examples[3] | | | | | | | |
| 1 | 3 | 1 | — | 62.6 | 3.3 | 6.3 | 8.4 |
| 2 | 0 | 4 | — | 47.8 | 4.2 | 13.0 | 7.3 |

[1] On the basis of the 5-methyluridine.
[2] Values obtained from the area ratio in HPLC.
[3] Results from direct bromoacetylation of 5-methyluridine.

From the table, it is clear that the present invention is excellent in the compounds and the production processes.

Effects of the Invention:

The nucleoside derivatives represented by the general formula (I) are useful intermediates for the synthesis of 2',3'-dideoxy-2',3'-didehydronucleoside derivatives typically represented by d4T, and thus, their novel commercially advantageous synthetic process is provided. Formation of by-products such as those brominated at the 5'-position, thymine, and the triacetyl derivatives are inhibited by using the first-mentioned nucleoside derivatives, and thereby, nucleoside derivatives such as 2'-deoxy-2'-bromo-3',5'-O-diacetyl-5-methyluridine and 2',3'-dideoxy-2',3'-didehydronucleoside derivatives are obtained in high yields.

What is claimed is:

1. A process for producing a nucleoside represented by formula (IV):

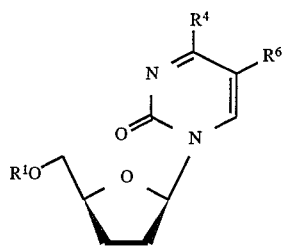 (IV)

wherein
- $R^1$ is selected from the group consisting of hydrogen, alkyl having from 1 to 19 carbon atoms, an acyl group having from 1 to 7 carbon atoms, and an organosilyl group;
- $R^4$ is selected from the group consisting of hydroxyl; amino; hydroxyl protected with a protecting group selected from the group consisting of acyl, organosilyl, and alkyl; and an amino group protected with a protecting group selected from the group consisting of acyl, organosilyl, and alkyl;
- $R^6$ is alkyl having from 1 to 12 carbon atoms or a halogen atom;

which comprises reacting a nucleoside represented by the formula (III):

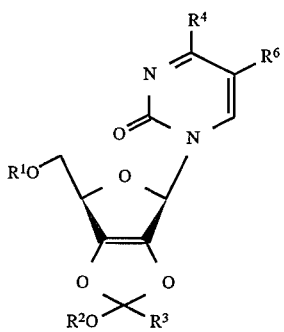 (III)

wherein $R^2$ is an alkyl having from 1 to 6 carbon atoms;
$R^3$ is selected from the group consisting of an alkyl group having from 1 to 6 carbon atoms and a phenyl group;
with a member of the group consisting of i) hydrogen bromide in acetic acid, (ii) acetyl bromide, and (iii) hydrogen bromide and acetyl bromide in acetic acid, to produce a nucleoside represented by the formula (VI):

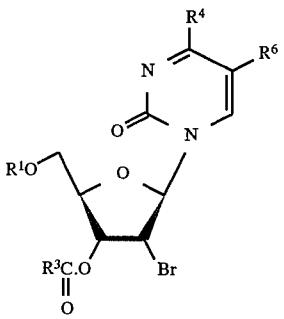 (VI)

and then reducing the nucleoside of formula (VI) with zinc to produce the nucleoside of formula (IV) above.

2. A process for producing a nucleoside according to claim 1, which further comprises removing the zinc moiety from the reaction mixture with sodium ethylenediaminetetraacetate subsequent to the reduction of the nucleoside of formula (VI).

3. A process for producing a nucleoside represented by the formula (VI):

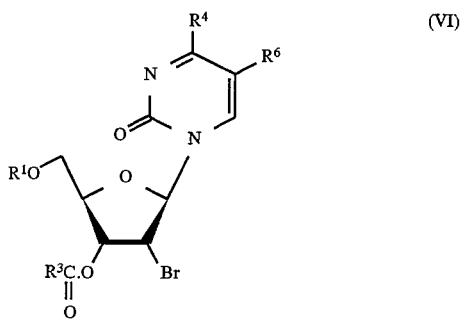 (VI)

wherein $R^1$ is selected from the group consisting of hydrogen, alkyl having from 1 to 19 carbon atoms, acyl having from 1–7 carbon atoms, and organosilyl;

$R^3$ is selected from the group consisting of alkyl having from 1 to 6 carbon atoms and a phenyl group;

$R^4$ is selected from the group consisting of hydroxyl; amino; hydroxyl protected with a protecting group selected from the group consisting of acyl, organosilyl, and alkyl; and an amino protected with a group selected from the group consisting of acyl, organosilyl, and alkyl;

$R^6$ is alkyl having from 1 to 12 carbon atoms or halogen;

which comprises reacting a nucleoside represented by formula (III) below:

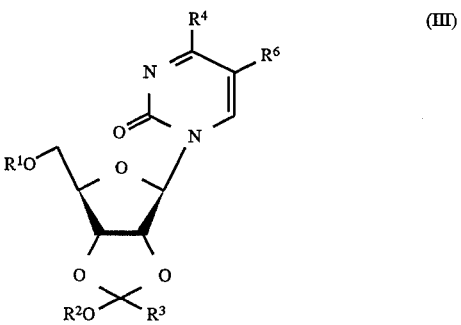 (III)

wherein $R^2$ is alkyl having from 1 to 6 carbon atoms;

with a reactant selected from the group consisting of (i) hydrogen bromide in acetic acid, (ii) acetyl bromide, and (iii) hydrogen bromide and acetyl bromide in acetic acid.

* * * * *